(12) United States Patent
Daub et al.

(10) Patent No.: US 9,816,085 B2
(45) Date of Patent: Nov. 14, 2017

(54) DEVICES, METHOD AND SYSTEM EMPLOYABLE FOR LYSING

(71) Applicant: Robert Bosch GmbH, Stuttgart (DE)

(72) Inventors: Martina Daub, Weissach (DE); Jochen Rupp, Stuttgart (DE); Peter Rothacher, Bruchsal (DE)

(73) Assignee: Robert Bosch GmbH, Stuttgart (DE)

( * ) Notice: Subject to any disclaimer, the term of this patent is extended or adjusted under 35 U.S.C. 154(b) by 161 days.

(21) Appl. No.: 14/062,722

(22) Filed: Oct. 24, 2013

(65) Prior Publication Data

US 2014/0120599 A1 May 1, 2014

(30) Foreign Application Priority Data

Oct. 25, 2012 (DE) .......................... 10 2012 219 575

(51) Int. Cl.
*A61B 10/00* (2006.01)
*C12N 13/00* (2006.01)
*C12N 1/06* (2006.01)
*C12M 1/00* (2006.01)

(52) U.S. Cl.
CPC ............. *C12N 13/00* (2013.01); *C12M 47/06* (2013.01); *C12N 1/066* (2013.01)

(58) Field of Classification Search
CPC ...................................................... A61N 1/00
See application file for complete search history.

(56) References Cited

U.S. PATENT DOCUMENTS

| 6,686,195 | B1 | 2/2004 | Colin et al. |
| 6,881,541 | B2 * | 4/2005 | Petersen ................. B01L 3/502 |
| | | | 435/259 |
| 7,785,868 | B2 * | 8/2010 | Yuan ................... B01F 11/0266 |
| | | | 241/2 |
| 2004/0076546 | A1 * | 4/2004 | Bissett ................... G01N 21/03 |
| | | | 422/68.1 |
| 2006/0158956 | A1 * | 7/2006 | Laugharn et al. ............ 366/127 |
| 2006/0191424 | A1 | 8/2006 | McLoughlin et al. |
| 2007/0231346 | A1 | 10/2007 | Babaev |

FOREIGN PATENT DOCUMENTS

| CN | 202576411 U | 12/2012 |
| EP | 1 359 415 A1 | 11/2003 |
| EP | 2 065 085 A1 | 6/2009 |
| JP | 6-305703 A | 11/1994 |
| WO | 99/28742 A1 | 6/1999 |

* cited by examiner

*Primary Examiner* — Jyoti Nagpaul
(74) *Attorney, Agent, or Firm* — Maginot, Moore & Beck LLP

(57) ABSTRACT

A device configured for lysing a sample includes a holding element configured to hold an energy-transmitting element such that the holding element lies around the held part of the energy-transmitting element and envelops the held part of the energy-transmitting element and/or that the holding element lies against the held part of the energy-transmitting element. The holding element is further configured to cause lysis with the energy-transmitting element when the holding element is immersed into the sample to be subjected to lysis or comes into contact with the sample to be subjected to lysis. A method includes inserting the energy-transmitting element into the holding element. A system configured for lysing a sample by way of ultrasound includes the device and the energy transmitting element.

14 Claims, 10 Drawing Sheets

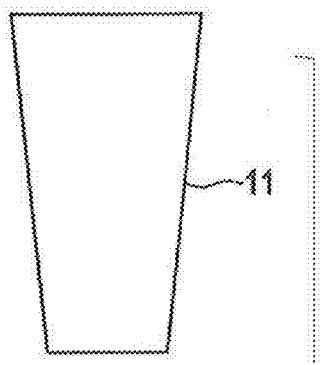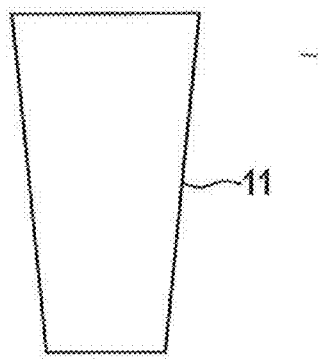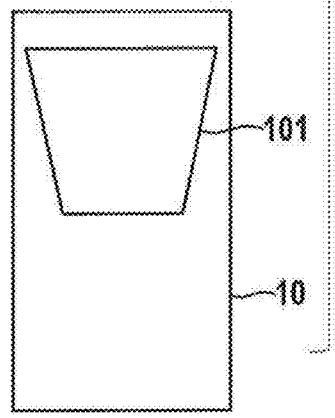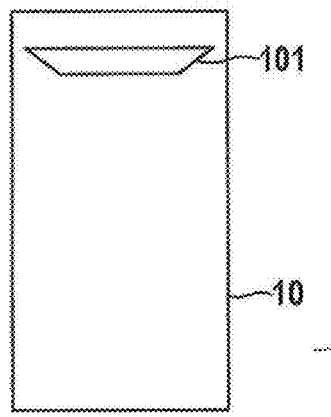
Fig. 1A
Fig. 1B

DEVICES, METHOD AND SYSTEM EMPLOYABLE FOR LYSING

This application claims priority under 35 U.S.C. §119 to patent application no. DE 10 2012 219 575.0, filed on Oct. 25, 2012 in Germany, the disclosure of which is incorporated herein by reference in its entirety.

BACKGROUND

The present disclosure relates to devices, a method and a system, which can be or are employed for lysing by means of ultrasound.

Lysis is well known as a method for dissolving cell membranes and hence for bringing about the breakdown of cells. Various methods can be employed for lysing, these also including lysing by means of transmission/application of the energy onto the sample or the lysate; this is well known. In the following text, the present disclosure will be explained in respect of the transmission by means of ultrasound. However, it should be noted in this context that the use of ultrasound as a type of energy is merely exemplary and that the present disclosure is not restricted thereto. That is to say it is also possible to employ other suitable energy transmissions, for example magnetic actuators.

By applying ultrasound onto a (sample or lysis) liquid with the cells to be dissolved, the cells are destroyed by shearing forces, which act on the cell membranes and/or the cell walls. An energy (ultrasound) transmitting element is usually immersed into the sample and irradiated by ultrasound. Coupling energy into the sample using the energy-transmitting element leads to cavitation and/or to the generation of shear forces in the sample, which then in the sample lead to the destruction or breakdown of the cells or the resistive cell membranes thereof.

The known methods for lysing by means of ultrasound however have a multiplicity of disadvantages. Contaminants can be introduced into the sample when immersing the energy-transmitting element. This is particularly the case if the energy-transmitting element is used a number of times and has to be cleaned after each lysis procedure. On the one hand, a sample can be contaminated by components of a previous sample. Furthermore, contamination by cleaning agents cannot be excluded. Furthermore, there is great manual outlay for preparing the lysis procedure in the case of each additional lysis. The outlay and the time requirements restrict the potential throughput of samples.

Some known methods attempt to rectify the aforementioned disadvantages by virtue of the lysis taking place in an ultrasonic bath. To this end, the sample to be lysed is held in a container which is immersed into a liquid of a bath irradiated by sound. This liquid irradiated by sound is also referred to as an ultrasonic bath. In the ultrasonic bath, the sample to be subjected to lysis is generally exposed to a constant ultrasonic field for a specific period of time. However, the energy transmission through the ultrasonic bath is significantly weaker. A further disadvantage lies in taking care of the liquid of the ultrasonic bath, since it can be contaminated by germs and/or algae. Furthermore, the liquid of the ultrasonic bath remains adhering to the container with the lysed sample and can lead to contaminants from the ultrasonic bath liquid and/or have an adverse effect on the ability to automate the whole process. Furthermore, lysis by means of an ultrasonic bath can have deficiencies in respect of an accurate reproducibility, since the reproducibility depends strongly on the position of the container with the sample to be lysed in the ultrasonic bath, with, additionally, the arrangement of the transducers around the ultrasonic pool also having to be maintained precisely in the case of repeated lysis. Furthermore, the distribution of the ultrasound is inhomogeneous in the ultrasonic bath. As a result, it is not possible to optimally meter the energy influx needed to lyse the cells (determined by the minimum energy) and to keep the components released during the lysis intact (determined by the maximum energy).

Hence there still is the need for lysis methods and lysis devices, by means of which the aforementioned disadvantages can be rectified.

SUMMARY

The disclosure proceeds from devices, a method and a system having the features of the disclosure. Further embodiments of the present disclosure can be gathered from the dependent claims.

The concept of the present disclosure consists of enabling the immersion of the energy-transmitting element (e.g. a resonator, a sonotrode or a horn, which are well known to transmit ultrasound) into a sample to be subjected to lysis or the contacting of the sample to be subjected to lysis or sample by the energy-transmitting element in such a way that the aforementioned disadvantages do not occur. To this end, a holding element is employed, which lies at least in part around and/or against the energy-transmitting element prior to the immersion into the sample. The holding element envelops at least part of the energy-transmitting element and/or the holding element lies against at least part of the energy-transmitting element in such a way that the holding element is in direct contact with the held part of the energy-transmitting element. Direct enveloping and/or direct lying thereon can be such that no sample liquid, no further liquids and/or interspaces are present between the holding element and the energy-transmitting element. Furthermore, the holding element and the held part of the energy-transmitting element (e.g. a sonotrode or a horn) can have a (substantially) gap-free contact. The enveloped part of the energy-transmitting element and/or the part of the energy-transmitting element against which the holding element lies corresponds to at least that part which is immersed into the sample. The enveloped part can also comprise the whole energy-transmitting element (such as e.g. a sonotrode or a horn). The envelope can be restricted in time. That is to say, the energy-transmitting element is enveloped by the holding element for a certain period of time, in particular for the period of time during which the lysis procedure is undertaken. The holding element can also lie against the held part of the energy-transmitting element for a restricted period of time. That is to say the holding element lies against the energy-transmitting element for a certain period of time, in particular for the period of time during which the lysis procedure is undertaken.

The present disclosure enables improved lysis. Thus, for example, the present disclosure enables contamination-free lysis of samples since the energy-transmitting element (at least partly) held in the holding element can, without direct contact to the sample to be subjected to lysis, be immersed into this sample or can establish a connection to this sample. Furthermore, lysis can be carried out with little manual outlay, as a result of which automation of the lysis process is also made possible. The present disclosure in particular enables good reproducibility of each lysis procedure. Furthermore, effective and optimum metering of the energy influx from the energy-transmitting element is ensured via the holding element. Hence, it is possible to open up or lyse the cells and, at the same time, keep the components of the cells intact. The present disclosure therefore offers optimum coupling of energy, which can be controlled well and effectively, into the sample to be lysed. The duration of the lysis procedure and/or the preparation of the lysis procedure is/are significantly reduced.

BRIEF DESCRIPTION OF THE DRAWINGS

In the following figures, the present disclosure will be described in more detail with reference to exemplary embodiments of the present disclosure. For the purpose of clarity, equivalent or similar elements are, in the figures, denoted by the same or similar reference signs.

FIGS. 1A-1D show a device embodied for use during lysis in accordance with one embodiment of the present disclosure;

DETAILED DESCRIPTION

Figure 1C:
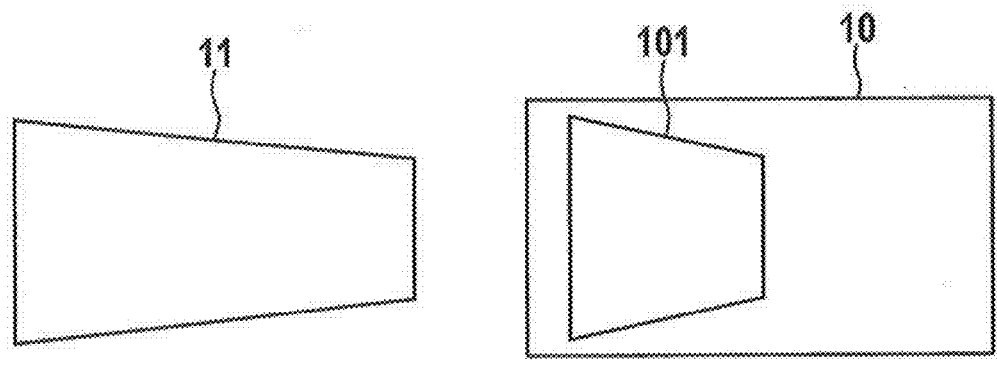

FIG. 1 shows a device 10 in accordance with a (general) embodiment of the present disclosure, wherein the device is embodied to be used for lysing a sample to be subjected to lysis (e.g. by means of ultrasound). Lysis can be performed by means of ultrasound. The device 10 comprises a holding element 101, which is embodied: to hold an energy-transmitting element 11 at least in part such that the holding element 101 lies around the held part of the energy-transmitting element 11 and envelops the held part of the energy-transmitting element 11 and/or that the holding element 101 lies against the held part of the energy-transmitting element 11; and to cause lysis with the energy-transmitting element 11, the held part of which is enveloped by the holding element 101 and/or against the held part of which the holding element 101 lies, when the holding element 101, which envelops the held part of the energy-transmitting element 11 and/or which lies against the held part of the energy-transmitting element 11, is immersed into a sample to be subjected to lysis or is in contact with the sample to be subjected to lysis. As already mentioned above, the device 10 enables contamination-free lysis of samples since the energy-transmitting element 11 (at least partly) held in the holding element 101 can, without direct contact to the sample to be subjected to lysis, be immersed into this sample or can establish a connection to this liquid. Furthermore, little manual outlay is required for lysis and between the lysis procedures of different samples following one another. Hence the device 10 also enables the automation and series-connection of a plurality of lysis processes. Moreover, the device 10 enables good reproducibility of each lysis procedure. Furthermore, effective and optimum metering of the energy influx is made possible from the energy-transmitting element 11 via the holding element 101. Hence, it is possible to open up or lyse the cells and, at the same time, keep the components of the cells intact. The device 10 leads to arbitrary combinations of the aforementioned positive effects. By way of example, the energy-transmitting element 11 can be embodied to transmit ultrasound. Here, the energy-transmitting element 11 can, for example, be a resonator, a sonotrode or a horn. The present disclosure enables various suitable embodiments of the energy-transmitting element 11 and various suitable ways of transmitting the energy.

In accordance with the present embodiment, the energy-transmitting element 11 and the holding element 101 establish a temporary connection, i.e. enveloping the held part of the energy-transmitting element 11 by the holding element 101 or laying the holding element 101 against the held part of the energy-transmitting element 11 is for a restricted period of time only. After the lysis procedure, the energy-transmitting element 11 or the appropriate held part of the energy-transmitting element 11 is guided out of the holding element. The contact between the energy-transmitting element 11 and the holding element 101 is broken apart after completion of the lysis procedure (e.g. by pulling the energy-transmitting element 11 out of the holding element 101 and/or by breaking the (direct) contact between the energy-transmitting element 11 and the holding element 101).

In accordance with the present exemplary embodiment, the holding element 101 is embodied to lie directly around and/or against the held part of the energy-transmitting element 11 and to be in direct contact with the held part of the energy-transmitting element 11. Direct contact means that the energy-transmitting element 11 and the holding element 101 contact directly (and substantially or wholly without gaps). That is to say, as a result of the direct contact, the holding element 101 and the energy-transmitting element 11 touch each other in such a way that there are no samples, liquids and/or materials between the two elements 101, 11.

In accordance with one embodiment, which can be combined with all of the explained embodiments, the holding element 101 is embodied as an elastic and deformable element. In accordance with the present embodiment, the holding element 101 is embodied as an elastic and deformable element and/or as a membrane. This enables good holding and contacting of the energy-transmitting element 11 by the holding element 101, as result of which the positive properties mentioned above in respect of the device 10 are amplified. The holding element 101 can, at least in part, have an elastic and deformable design. That is to say, it can be elastic and deformable everywhere or at least a specific part of the holding element 101 can be elastic and deformable. As a result, the holding element 101 can have a flexible design. Improved adaptability to the energy-transmitting element 11 can be achieved in the process. Furthermore, the function of being coated directly thereon and/or of lying directly thereon can also be supported in improved manner. By way of example, it may be expedient for an improved fit to the energy-transmitting element 11 that the holding element 101 is more solid and optionally not or less elastic or not or less deformable in at least one part, while the elasticity and deformability properties are given in at least one further part. The better the holding element 101 fits to the energy-transmitting element 11, the better the direct contact is formed between the two elements 101, 11, which in turn amplifies every single one of the further advantages mentioned in the application (e.g. better energy coupling can be ensured, etc.). In accordance with the present embodiment, the energy-transmitting element 11 is a sonotrode or a horn. This enables good energy coupling and the irradiation in the sample liquid by sound, which likewise supports the aforementioned positive properties. As already known, the sonotrode and the horn permit irradiating the sample liquid by means of ultrasound since both the sonotrode and the horn are ultrasound-transmitting elements.

In the explanation of the following embodiments, the term "holding element" continues to be used. However, it should be noted that the present disclosure in general also understands an "elastic and deformable element" and/or "membrane" by the term "holding element" and that the present application also specifies the "elastic and deformable element" and the "membrane" every time the "holding element" is specified.

In the explanations relating to the present disclosure, the term "energy-transmitting element" is likewise employed. Here, it should be noted that the present disclosure in general also understands a sonotrode or a horn under the term "energy-transmitting element". Here, the sonotrode or the horn transmits ultrasound as energy. It should also be noted that further energy-transmitting elements can also be applied by the present disclosure. Therefore the present disclosure also specifies a sonotrode, a horn or another suitable energy-transmitting element every time the energy-transmitting element is specified.

Figure 1D:
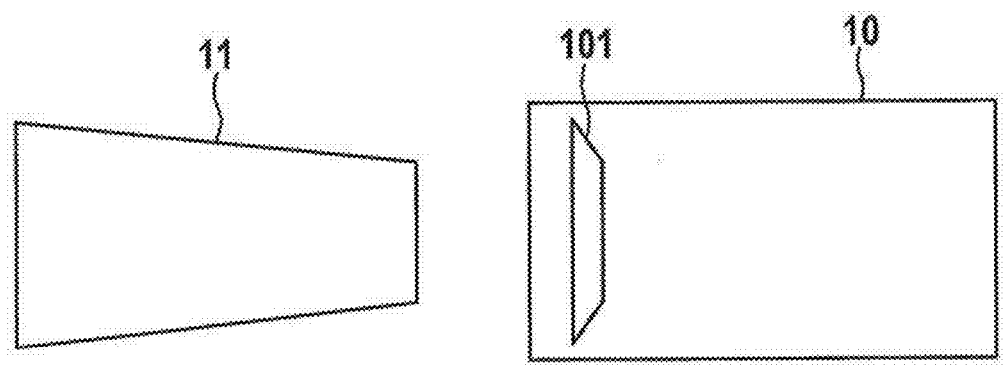

FIG. 1 is composed of four Sub-FIGS. 1A to 1D. In accordance with the embodiments of FIGS. 1A and 1C, the holding element 101 is preformed in respect of the shape of the energy-transmitting element 11. This enables good holding of the energy-transmitting element 11, as result of which the aforementioned positive properties in respect of the device 10 are amplified. Holding the energy-transmitting element 11 in this case comprises enveloping the energy-transmitting element 11 by the holding element 101 and/or laying the holding element 101 against the energy-transmitting element. In particular, direct contact between the holding element 101 and the energy-transmitting element 101 can be made possible. In accordance with embodiments in FIGS. 1B and 1D, the holding element 101 is not preformed. However, the positive properties of FIGS. 1A and 1C can also be achieved here as a result of the elasticity.

The holding element 101 (i.e. the elastic and deformable element or membrane 101 as well) can consist of a polymer or of elastomer (e.g. rubber). By way of example, the polymer can be PC, COP, COC, PP, PE, PMMA, PET, PEN, silicone or TPE. These materials offer good properties of elasticity and deformability, which strengthens the aforementioned positive effects.

Here, the holding element 101 can typically have the following thickness: 10 µm to 400 µm; 50 µm to 1 mm; 300 µm to 400 µm; or 375 µm. Overall, the thickness can be between 10 µm and 1 mm. As a result of these thicknesses, the properties of elasticity and deformability of the holding element 101 are supported, which likewise strengthens the aforementioned positive effects.

As shown in Sub-FIGS. 1A to 1D, the energy-transmitting element 11 may be inserted into the holding element 101 from different directions and at different angles. Here, FIG. 1A and FIG. 1B show the insertion from above in an exemplary manner and FIG. 1C and FIG. 1D show the insertion from the side in an exemplary manner.

Figure 2A:
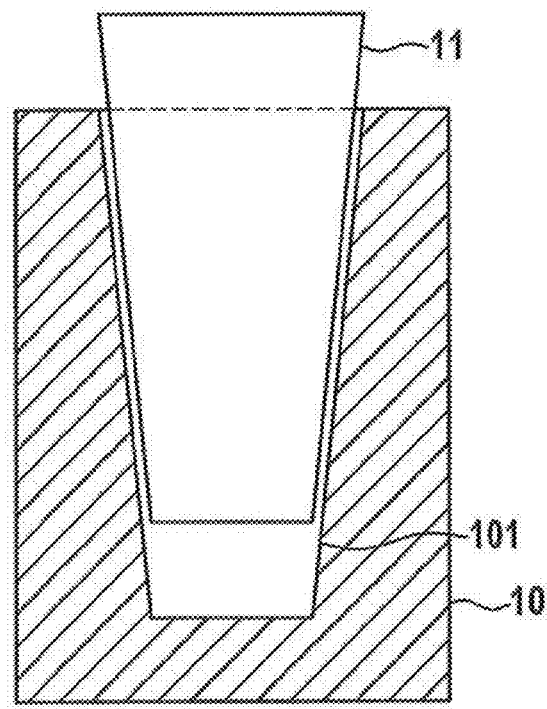
FIGS. 2A and 2B show the insertion of the energy-transmitting element into the holding element in accordance with one embodiment of the present disclosure.
Figure 2B:
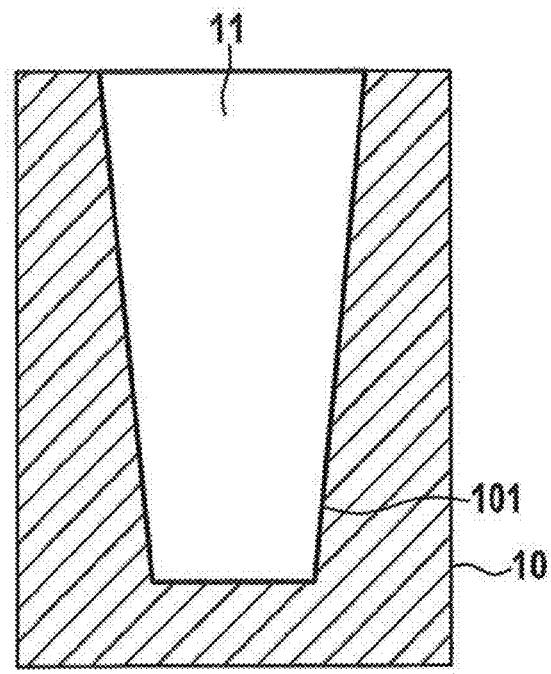

FIG. 2 shows the insertion of the energy-transmitting element 11 into the holding element 101 or in accordance with one embodiment of the present disclosure. In accordance with the present embodiment, the holding element 101 is preformed. However, the embodiment can also be applied to holding elements 101 that are not preformed. In FIG. 2A, the energy-transmitting element 11 is almost inserted into the holding element 101. FIG. 2B shows how the holding element 101 envelops the energy-transmitting element 11 after the insertion and/or lies against the energy-transmitting element 11 after insertion. Here, the two elements 101, 11 are in direct (and substantially or wholly gap-free) contact with one another after the insertion. Hence, this is direct enveloping by the holding element 101 and/or direct lying of the holding element 101 against the energy-transmitting element 11. In FIG. 2B, the holding element 101 completely holds the energy-transmitting element 11. Similarly, it is also possible for only part of the whole energy-transmitting element 11 to be held (partial holding).

For the purposes of insertion as depicted above in an exemplary manner, the holding element 101 is designed to at least partly hold the energy-transmitting element 11 by one of the following steps: by applying external contact pressure on the energy-transmitting element 11; by applying positive pressure in a lysis container with the sample to be subjected to lysis; by combined application of positive pressure around a lysis container with the sample to be subjected to lysis and a counteracting force, applied from the outside, on the energy-transmitting element 11; or by applying negative pressure around the energy-transmitting element 11. Hence a flexible configuration for holding the energy-transmitting element 11 in the holding element 101 is rendered possible. The selection of the respective method for holding can be determined depending on the surroundings and the further design of the device 10.

During the at least partial holding of the energy-transmitting element 11, the holding element 101 can arch in the direction of the energy-transmitting element 11 and, in the process, establish a direct and/or (substantially) gap-free contact with the held part of the energy-transmitting element 11.

In the following text, further embodiments of the device 10 are explained. In this respect, it should be noted that the above-described properties and positive effects also apply to the following embodiments unless something else or specific is explicitly mentioned in respect of one of the following embodiments. It should furthermore be noted that the properties and features explained in respect of the following embodiments complement the properties and features of the device 10 explained above.

As can be gathered from the following embodiments, the device 10 can, for example, be one of the following: a cover for a lysis container; an adapter for a lysis container; a lysis container; or a lab on a chip. In accordance with one embodiment of the present disclosure, the lab on a chip 10 has an integrated cartridge for processing analyses which the holding element 101 can comprise. In accordance with a further embodiment, the device 10 can be the aforementioned cartridge for processing analyses. As a result of these embodiments, an implementation of the present disclosure is enabled, which is flexible and adapted to the conditions and requirements.

Figure 3A:
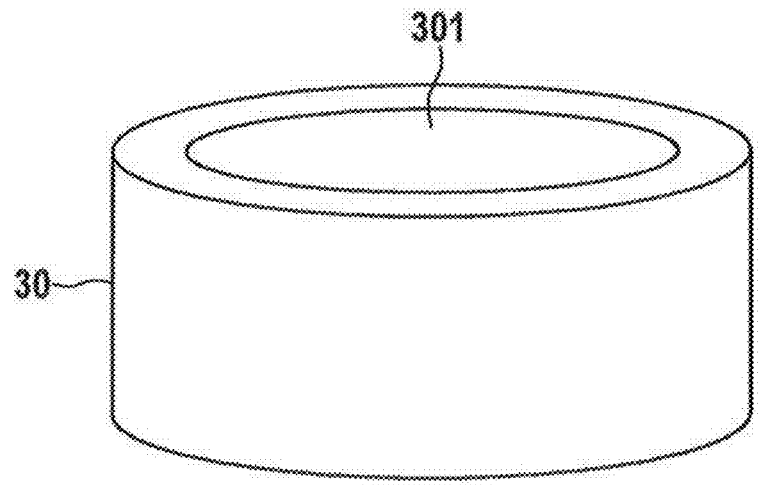
FIGS. 3A and 3B show a device embodied for use during lysis in accordance with one embodiment of the present disclosure.
Figure 3B:
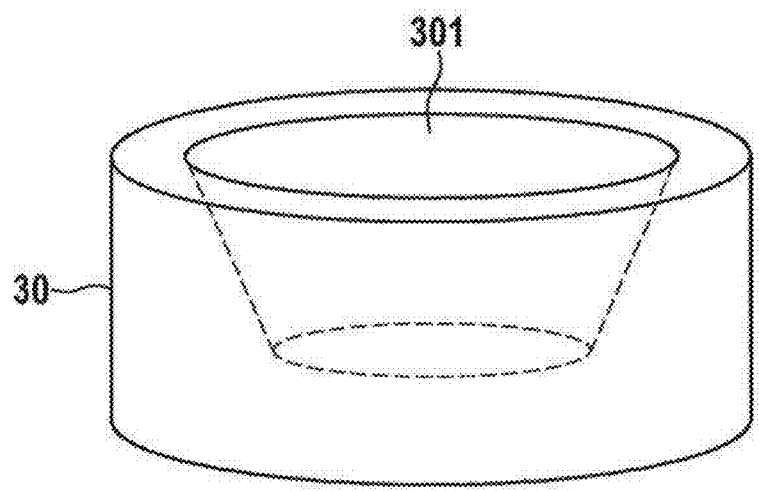
Figure 4:
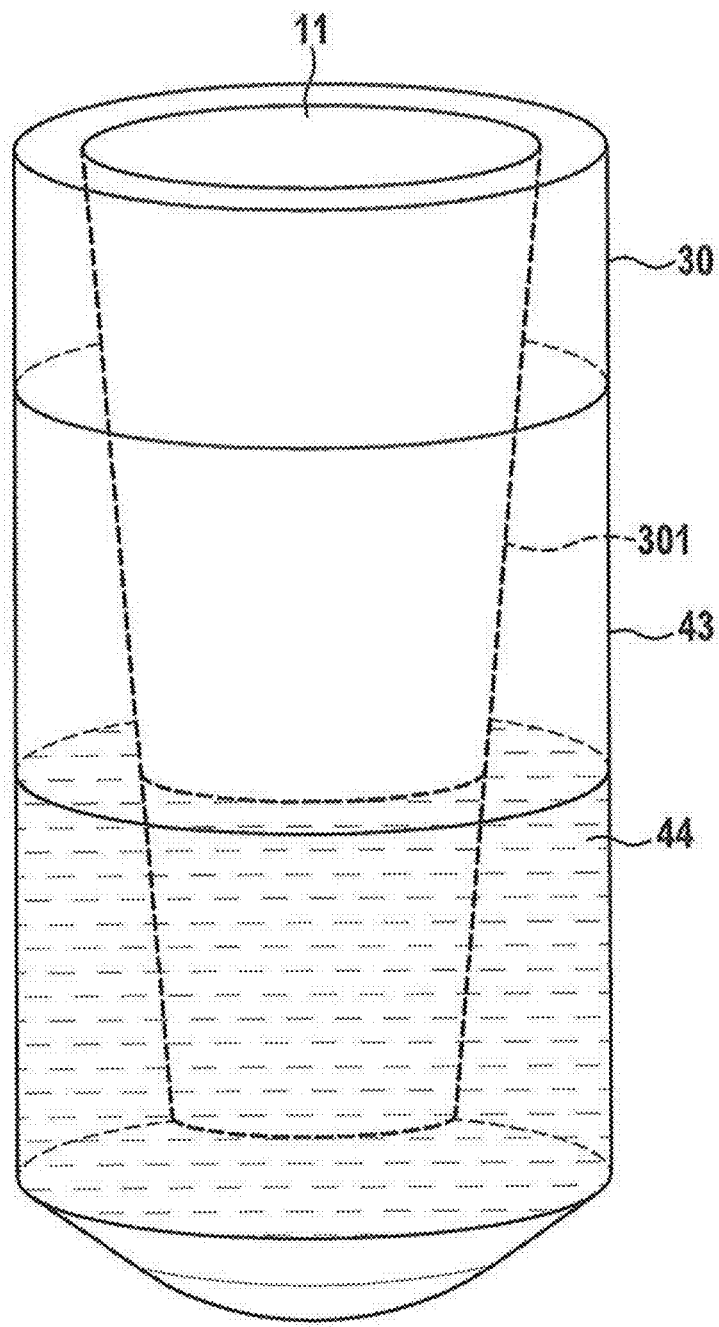
FIG. 4 shows the device in accordance with the embodiment when the holding element at least partly holds the energy-transmitting element for lysing a sample.

FIG. 3 shows a device 30 in accordance with one embodiment of the present disclosure, wherein the device 30 is embodied for use during lysis by means of ultrasound and is a cover or an adapter for a lysis container. FIG. 4 shows the device 30 when the holding element 301 of the device 30 at least partly holds the energy-transmitting element 11 for lysing a sample 44. Here, the sample 44 is situated in a lysis container 43, which is connected to the cover or adapter 30. Once the holding element 301 (at least partly) holds the energy-transmitting element 11 (see FIG. 4), the holding element 301, which (directly) envelops the energy-transmitting element 11 and/or which (directly) lies against the energy-transmitting element, protrudes into the sample 44 to be subjected to lysis. The sample 44 can be subjected to lysis by the enveloped energy-transmitting element 11. As already mentioned, the lysis can, for example, take place by means of ultrasound transmission by the energy-transmitting element 11.

In accordance with this embodiment, the energy-transmitting element 11 is separated by the cover or adapter 30 from the sample liquid 44, which contains the material to the opened up or lysed. The cover or adapter 30 has the holding element 301, which can be preformed in respect of the shape of the energy-transmitting element 11 (see FIG. 3B) or which can have a substantially flat or planar design (see FIG. 3A). The holding element 301 assumes the required shape for (at least partly) coating the energy-transmitting element 11 and/or for (at least partly) lying against the energy-transmitting element 11 by contact to the energy-transmitting element 301 and by the connection force (e.g. pressure, negative pressure, clamping and/or coating). The holding element 301 can consist of a polymer or elastomer (e.g. rubber) and can, for example, have a thickness of between 10 µm and 400 µm. The holding element 301 can (directly) enclose at least the front part of the energy-transmitting element 11 and hence realize a (direct) coat for the latter. The temporary connection between the energy-transmitting element 11 and the external side of the cover or of the adapter 30 (or the holding element 301) can be imparted by various mechanisms, for example by: applying external contact pressure on the energy-transmitting element 11 (e.g. by means of springs, stepping motor(s), clamp(s), press fit(s)); applying positive pressure around the lysis container 43 combined with applying a counteracting force to the energy-transmitting element 11 from the outside; or applying negative pressure around the energy-transmitting element 11.

Furthermore, the cover or the adapter 30 can be embodied in such a way that the cover or the adapter 30 exhibits a temporary or (securely) sealing function between the sample liquid 44 and the outside world (i.e. outer surroundings of the lysis container 43 and of the cover or adapter 30). This can also be realized by various mechanisms, for example: the holding element 301 itself is embodied to carry out the sealing function; and/or the element 301 is a rigid element of the cover or of the adapter 30, which can be connected to the lysis container 43, for example by screwing, clamping and/or latching.

The cover or the adapter 30 can be embodied in such a way that they can be plugged and/or screwed onto commercially available lysis containers 43 or in such a way that they can be pressed onto commercially available lysis containers 43 during the actuation. As already mentioned previously, the cover or the adapter 30 can provide a sealing function. The cover or the adapter 30 can be embodied as a disposable article.

Figure 5:
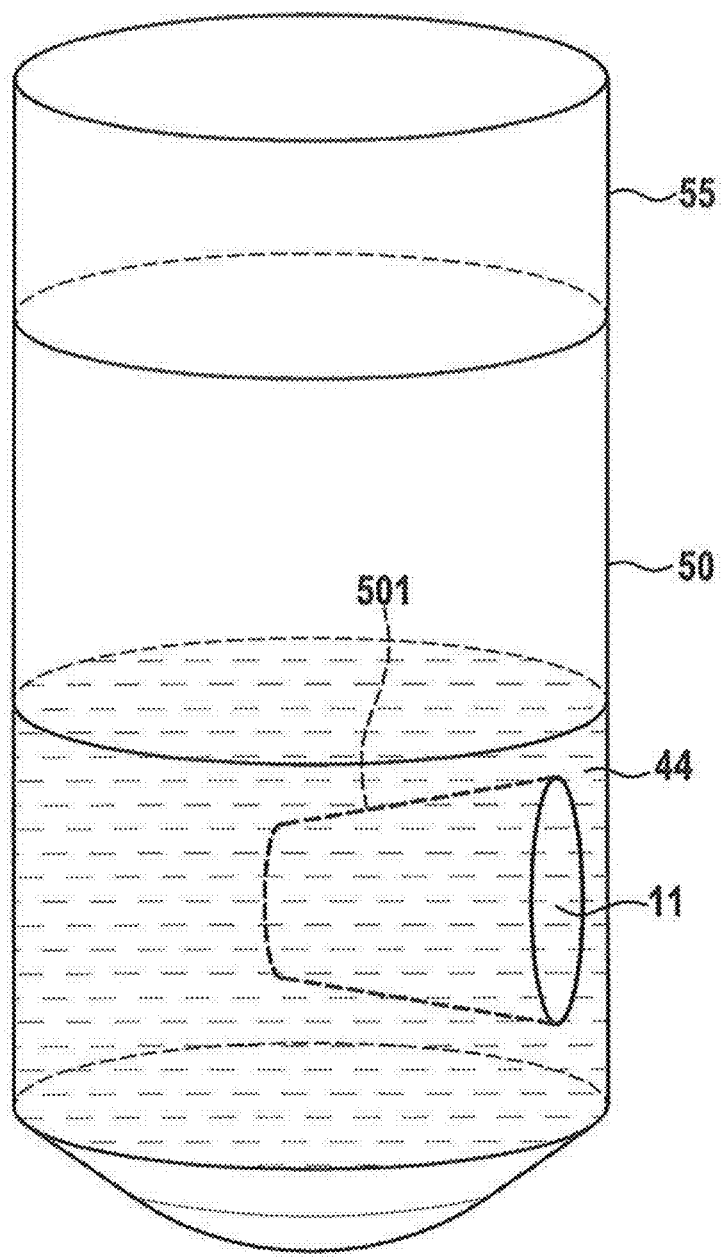
FIG. 5 shows a device embodied for use during lysis in accordance with one embodiment of the present disclosure.

FIG. 5 shows a device 50 in accordance with one embodiment of the present disclosure embodied for lysing (a sample to be subjected to lysis), wherein the device 50 is a lysis container. By way of example, the lysis can be performed by means of ultrasound. FIG. 5 shows a situation in which the energy-transmitting element 11 is inserted into the holding element 501 of the lysis container 50. It should be noted that the properties, features and effects, which are explained above or below in respect of further embodiments and which are not explicitly in opposition to or different from the properties, features and effects of the present embodiment, complement the present embodiment, even if this is not explicitly mentioned for reasons of keeping the present description short.

In accordance with the present embodiment, the holding element 501 is (fixedly) inserted into the lysis container 50 and is immersed (without air bubbles) into the sample 44 to be lysed by negative pressure around the energy-transmitting element 11 and/or by positive pressure in the lysis container 50. The holding element 501 therefore constitutes an interface to the externally applied energy-transmitting element 11. The connection between the holding element 501 and the energy-transmitting element 11 is realized as illustrated above in respect of the preceding embodiments.

By way of example, the holding element 501 can be integrated into the lysis container 50 by one of the following methods:
laser beam welding, laminating, ultrasound welding, adhesive bonding and/or film thermoforming.

The lysis container 50 can be connected to a cover 55 in order to avoid external influences acting on the sample liquid 44. Furthermore, the lysis container 50 can also be embodied as disposable container.

FIG. 6 shows a device 60 in accordance with one embodiment of the present disclosure embodied for lysing (a sample to be subjected to lysis), wherein the device 60 is a lysis container and wherein lysis can be performed by means of ultrasound. It should be noted that the properties, features and effects, which are explained above or below in respect of further embodiments and which are not explicitly in opposition to or different from the properties, features and effects of the present embodiment, complement the present embodiment, even if this is not explicitly mentioned for reasons of keeping the present description short.

The lysis container 60 is arranged in a lysis chamber 66. The side/wall of the lysis container facing the energy-providing element 11 is (at least in part) embodied as a holding element 601. The holding element 601 can be a polymer membrane. By way of example, the polymer membrane 601 can consist of PC, COP, COC, PP, PE, PMMA, PET, PEN, elastomer (e.g. rubber, silicone, TPE). Furthermore, the polymer membrane 601 can have a thickness of between 10 µm and 1 mm. By way of example, if the poly-membrane 601 consists of PC, COP or COC, it can, for example, have a thickness of between 300 µm and 500 µm. Compared to other embodiments, stiffer membranes, which have less damping, can be used in accordance with the present embodiment.

Figure 6A:
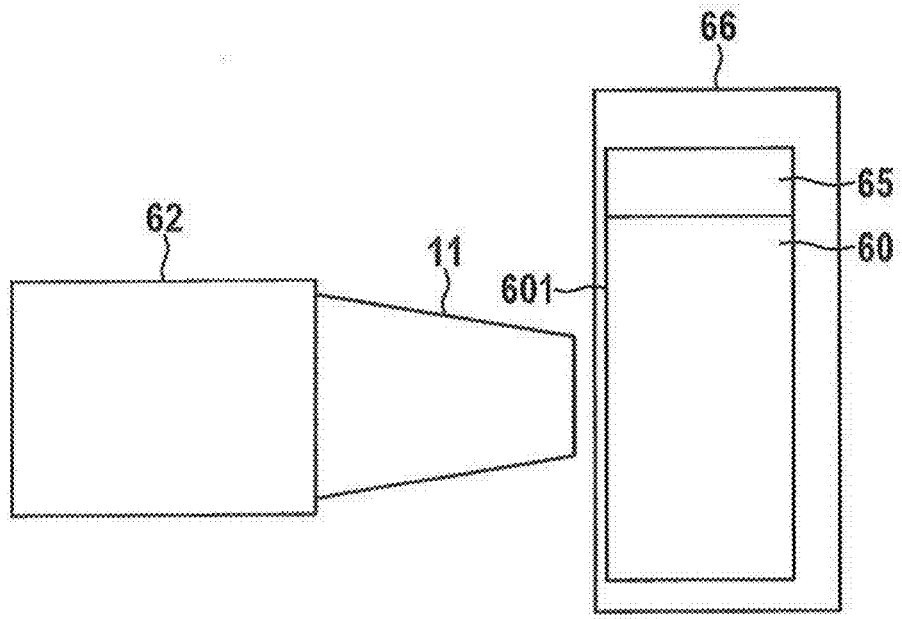
FIGS. 6A and 6B show a device embodied for use during lysis in accordance with one embodiment of the present disclosure.
Figure 6B:
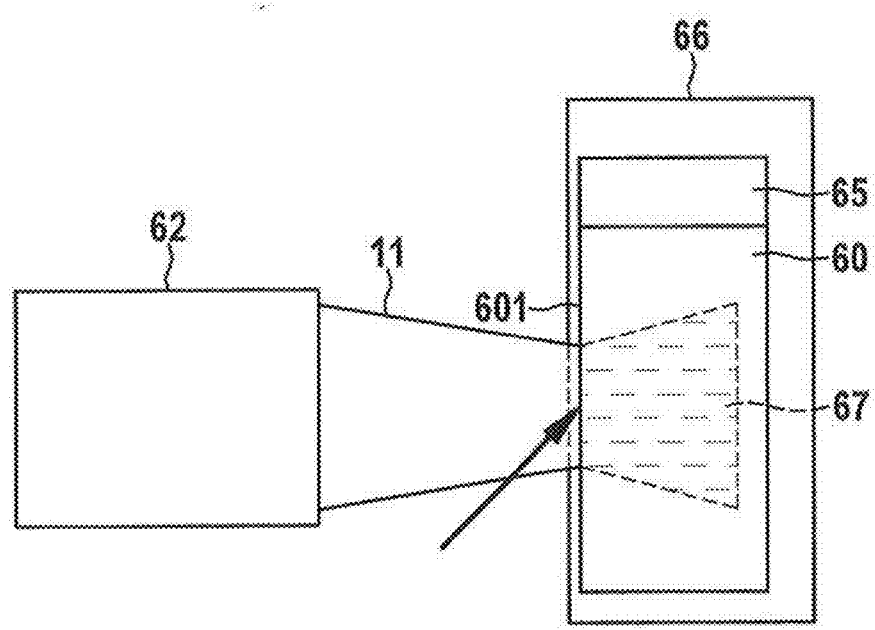

The energy-transmitting element 11 is laid against the holding element 601 or the energy-transmitting element 11 is brought into the vicinity of the holding element 601 (see FIG. 6A). The gap between the two elements 11, 601 can, for example, have a width of approximately 0.1 mm. Following this, pressure (e.g. air or liquid content) is applied to the lysis container 60. By way of example, the absolute pressure can be between 0.5 bar and 2 bar in this case. In the process, positive pressure is generated in the lysis container 60, as a result of which the holding element 601 arches in the direction of the energy-providing element 11 and establishes a (substantially) gap-free contact with the latter (see FIG. 6B). In FIG. 6B, the (substantially) gap-free contact is marked by an arrow between the two elements 11 and 601. The application of pressure is clarified by the thicker arrow which is directed to the lysis chamber 66 or to the lysis container 60.

By way of example, the energy-transmitting element 11 can be embodied as a resonator, sonotrode, horn, lambda half or lambda transducer.

The ultrasound generator (not shown) is thereupon actuated for up to several minutes in order to lyse the sample liquid contained in the lysis container 60. By way of example, the ultrasound generator can be actuated with 30 kHz, with lower or higher frequencies ranging from 20 kHz to 1 MHz likewise being possible. More DNA fragmentation was observed at 40 kHz; there is more noise pollution at 20 kHz. Here, the energy influx can be continuous or pulsed. The ultrasound generator is coupled to the ultrasound transducer 62, which in turn transmits sound to the energy-providing element 11. By irradiating the sample liquid in the lysis container 60 with ultrasound, shearing forces and/or cavitation 67 is/are generated, by means of which lysing of the sample liquid in the lysis container 60 is brought about.

The sample liquid subjected to lysis can subsequently be removed from the lysis chamber 66 and processed further in a lab on a chip. To this end, an inlet opening (supply of optional additional lysis medium) and an outlet opening (e.g. for the further treatment) may be required. In FIG. 6, this is covered and sealed in an exemplary manner by a cover 65.

Figure 7A:
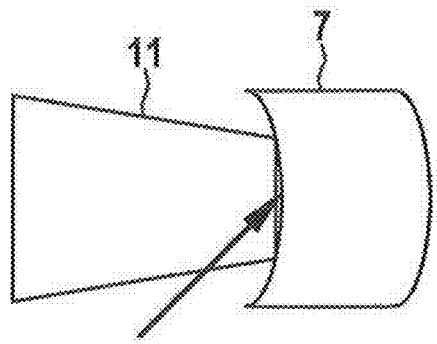
FIG. 7A shows the formation of a contact, afflicted by a gap, to the energy-providing element in accordance with known methods for lysis with energy-providing elements.
Figure 7B:
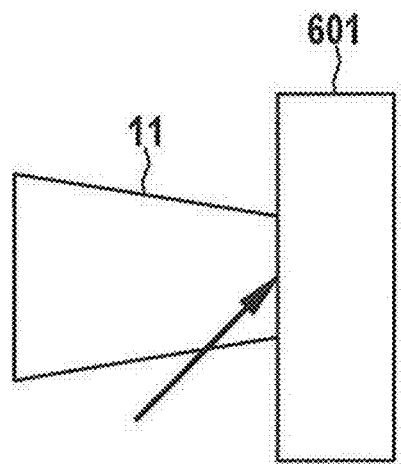
FIG. 7B shows the gap-free formation of a contact to the energy-providing element in accordance with one embodiment of the present disclosure.

Using the present embodiment, it is also possible to employ flatter lysis containers 60, which in other lysis methods entail the disadvantage of results which are difficult to reproduce since flat container walls bend in the case of contact pressure by an energy-transmitting element 11 in such a way that the contact between the container wall and the energy-transmitting element 11 is discontinued in the center of the energy-transmitting element 11; see FIG. 7A, in which a gap (marked by an arrow) is created when establishing contact between the energy-transmitting element 11 and the container wall 7. FIG. 7B shows the gap-free establishment of contact in accordance with the present embodiment. When using less elastic holding elements 601 (e.g. polymer membranes), the established contact becomes ever worse, the higher the contact pressure of the energy-transmitting element 11 is selected to be on the wall of a lysis container. The annular contact areas resulting in that case can easily overheat when actuated by ultrasound and the coupling becomes not reproducible. This phenomenon becomes ever more critical, the thinner the wall of the lysis container or the thinner the holding element 601 is and the less flexible (e.g. the thicker) the holding element 601 (e.g. membrane) is.

Using the present embodiment, this coupling problem is achieved by virtue of a flat energy-transmitting element being applied in the vicinity of the holding element 601 of the lysis container 60 and the lysis container 60 being impinged upon with pressure (e.g. air or liquid content) in such a way that the holding element 601 is laid against the energy-transmitting element 11 and the gap between the energy-transmitting element 11 and the lysis container 60 is reliably closed. The force fit between the two elements 11, 601 established thus leads to energy (e.g. ultrasound) being coupled in reliably. Furthermore, this also allows compensation for wedge errors between the energy-transmitting element 11 and the lysis container 60 or the holding element 601 (e.g. due to holding tolerances or cartridge manufacturing tolerances). Moreover, for an optimum force fit, the geometry of the tip of the energy-transmitting element, which encounters the holding element when it is held), can also be designed for the geometry of the holding element under pressure.

The lysis container 60 can also be provided as a disposable container.

In summary, the positive effects of the present embodiment are at least as follows: in accordance with the present embodiment, it is also possible to use flat holding elements 601. The holding element 601 can easily be coupled to the energy-transmitting element 11. The embodiment enables with great reliability the creation of cavitation and/or shearing forces for the purposes of lysis. It is possible to use very thin holding elements 601 (e.g. membranes), which for example can have a thickness of between 10 μm and 1 mm and can, in the process, for example have a thickness of between 200 μm and 500 μm, 50 μm and 1 mm. Flat holding elements 601 (e.g. membranes) can be cooled over their entire area over the surface of the energy-transmitting element 11 and are more durable than holding elements 601 (e.g. membranes) which only contact at points or in an annular manner. Lysis can be carried out quickly and in a material-saving manner.

Figure 8:
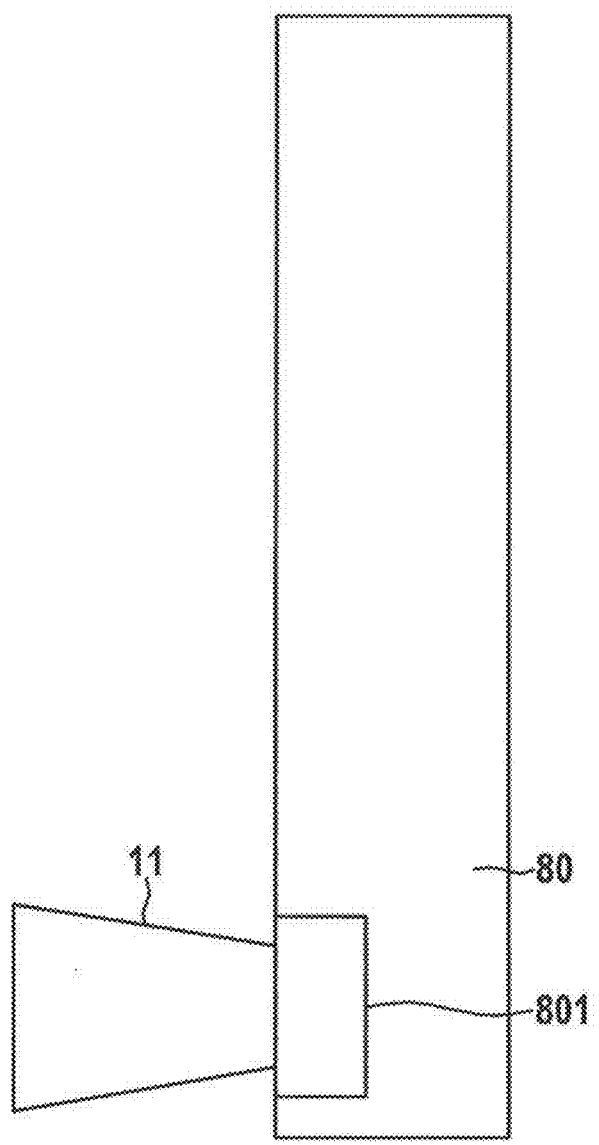
FIG. 8 shows a device embodied for use during lysis in accordance with one embodiment of the present disclosure.

FIG. 8 shows a device 80 in accordance with one embodiment of the present disclosure embodied for lysing (a sample to be subjected to lysis), wherein the device 80 is a lab on a chip ("lab-on-chip system"). By way of example, lysis can be performed by means of ultrasound. It should be noted that the properties, features and effects, which are explained above or below in respect of further embodiments and which are not explicitly in opposition to or different from the properties, features and effects of the present embodiment, complement the present embodiment, even if this is not explicitly mentioned for reasons of keeping the present description short. The lab on a chip 80 has a holding element 801 which, as described above, can be an elastic and deformable element and/or a membrane. The holding element 801 constitutes an interface of the lab on a chip 80 to an energy-transmitting element 11. The holding element 801 substantially has the same properties, features and effects as the holding elements 101, 301, 501, 601 explained above.

Figure 9:
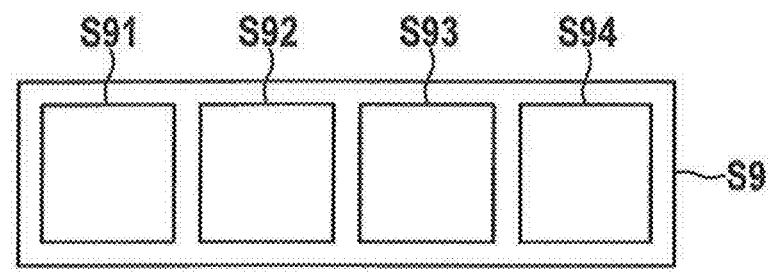
FIG. 9 shows the steps of a method for inserting an energy-transmitting element into a holding element for lysing a sample in accordance with one embodiment of the present disclosure.

In accordance with one embodiment of the present disclosure, FIG. 9 shows the steps of a method for inserting an energy-transmitting element 11 into a holding element 101, 301, 501, 601, 801. The method primarily has the step S9 of at least partly inserting an energy-transmitting element 11 into a holding element 101, 301, 501, 601, 801, wherein, as a result of the at least partial insertion, the holding element 101, 301, 501, 601, 801 at least partly holds the energy-transmitting element 11 in such a way the holding element 101, 301, 501, 601, 801 lies around the held part of the energy-transmitting element 11 and envelops the held part of the energy-transmitting element 11 and/or that the holding element 101, 301, 501, 601, 801 lies against the held part of the energy-transmitting element 11, wherein, as result of the at least partial insertion, the holding element 101, 301, 501, 601, 801 with the held energy-transmitting element 11 is provided for lysing a sample to be subjected to lysis. By way of example, lysis can be performed by means of ultrasound. Lysis by means of ultrasound is triggered by this step S9 when the energy-transmitting element 11, which is inserted into the holding element 101, 301, 501, 601, 801, is immersed into a sample to be lysed or is in contact with the sample to be lysed.

The at least partial insertion S9 is carried out in such a way that the holding element 101, 301, 501, 601, 801 lies directly around and/or against the held part of the energy-transmitting element 11 and is in direct ((substantially) gap-free) contact with the held part of the energy-transmitting element 11.

In accordance with the method of the present embodiment, the at least partial insertion S9 can be carried out by one of the following options: by applying external contact pressure on the energy-transmitting element 11 in step S91; by applying positive pressure in a lysis container 43, 50, 60 with a sample 44 to be subjected to lysis in step S92; by combined application of positive pressure around a lysis container 43, 50, 60 with a sample 44 to be subjected to lysis and a counteracting force, applied from the outside, on the energy-transmitting element 11 in step S93; or by applying negative pressure around the energy-transmitting element 11 in step S94.

In step S9, the at least partial insertion can be carried out in such a way that the holding element 101, 301, 501, 601, 801, when at least partly holding the energy-transmitting element 11, arches in the direction of the energy-transmitting element 11 and establishes a (substantially) gap-free contact with the held part of the energy-transmitting element 11.

Further details in respect of the steps of the method in FIG. 9 can be gathered from the embodiments above.

Figure 10:
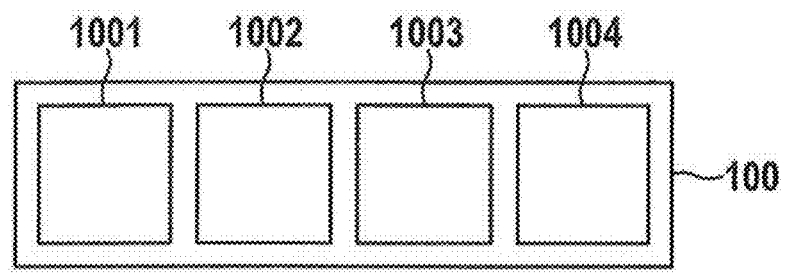
FIG. 10 shows, in accordance with one embodiment, a device which is embodied to carry out the aforementioned method.

In accordance with one embodiment, FIG. 10 shows a device 100 which is embodied to carry out the method sketched out above. The device 100 is substantially embodied to carry out the at least partial insertion of the energy-transmitting element 11 into the holding element 101, 301, 501, 601, 801 in accordance with step S9 of the method sketched out above. Here, the device 100 can comprise the following modules/elements: the module/element 1001, which is embodied to carry out step S91 of the method sketched out above; the module/element 1002, which is embodied to carry out step S92 of the method sketched out above; the module/element 1003, which is embodied to carry out step S93 of the method sketched out above; and/or the module/element 1004, which is embodied to carry out step S94 of the method sketched out above.

In view of the figures explained above, it furthermore becomes clear that the present disclosure also comprises a system comprising the device 10, 30, 50, 60, 80, which is embodied for use when lysing a sample to be subjected to lysis, and comprising the energy-transmitting element 11.

The embodiments explained above with the specific aspects explained there can be combined with one another. In particular, the properties, functions and/or embodiments of the holding elements 101, 301, 501, 601, 801 are the same or at least similar. The properties and functions described in one embodiment can be applied to further embodiments since the following exemplary embodiments take over the previously described properties and functions and/or are built-up thereon for reasons of a clear illustration of the present disclosure. The present disclosure enables contamination-free and reproducible lysing. Furthermore, lysis can be undertaken in a quick and efficient manner. Moreover, the present disclosure ensures reliable coupling of the energy (e.g. ultrasound) into the sample to be lysed.

What is claimed is:

1. A device configured for lysing a sample to be subjected to lysis, comprising:
a lysis container for containing the sample to be subjected to lysis, the container having a cover to enclose the sample within the container; and
a holding element configured to hold an energy-transmitting element such that the holding element lies around a held part of the energy-transmitting element and envelops the held part of the energy-transmitting element,
the holding element further incorporated into one or more of the lysis container and the cover for the lysis container so that the holding element is at least partially immersed into the sample to be subjected to lysis,
wherein the energy-transmitting element is a sonotrode or a horn.

2. The device according to claim 1, wherein the holding element is configured to lie directly around and against the held part of the energy-transmitting element.

3. The device according to claim 1, wherein the holding element is configured as a membrane and/or is completely or at least partly elastic and deformable.

4. The device according to claim 3, wherein the membrane has a thickness of between 10 μm to 400 μm, 50 μm to 1 mm, or 300 μm to 400 μm.

5. The device according to claim 1, wherein the holding element is preformed in respect of the held part of the energy-transmitting element.

6. The device according to claim 3, wherein the membrane has a thickness of between 10 μm and 1 mm.

7. The device according to claim 3, wherein the holding element is configured so that the membrane arches in the direction of the energy-transmitting element and establishes a gap-free or substantially gap-free contact with the held part of the energy-transmitting element when pressure is applied to the sample within the container.

8. The device according to claim 1, wherein one or more of:
the holding element is configured to at least partly hold the energy-transmitting element by:
(i) applying external contact pressure on the energy-transmitting element;
(ii) applying positive pressure in a lysis container with the sample to be subjected to lysis;
(iii) combined application of positive pressure around a lysis container with the sample to be subjected to lysis and a counteracting force, applied from the outside, on the energy-transmitting element; or
(iv) applying negative pressure around the energy-transmitting element.

9. The device according to claim 1, wherein the holding element consists of a polymer or of elastomer.

10. The device according to claim 1, wherein said energy-transmitting element is configured to transmit energy directly to the sample within the lysis container.

11. A system, comprising:
an energy-transmitting element, wherein the energy-transmitting element is a sonotrode or a horn; and
a device configured to lyse a sample to be subjected to lysis, the device including;
a lysis container for containing the sample to be subjected to lysis, the container having a cover to enclose the sample within the container; and
a holding element configured to hold an energy-transmitting element such that the holding element lies around a held part of the energy-transmitting element and envelops the held part of the energy-transmitting element, the holding element further incorporated into one or more of the lysis container and the cover for the lysis container so that the holding element is to be at least partially immersed into the sample to be subjected to lysis.

12. The device according to claim 1, wherein the holding element is configured to hold at least part of the energy-transmitting element.

13. The system according to claim 11, wherein the device is a lab-on-a-chip configured to be placed in contact with the sample to be subjected to lysis.

14. The system according to claim 11, wherein said energy-transmitting element is configured to transmit energy directly to the sample within the lysis container.

* * * * *